Figure 1:
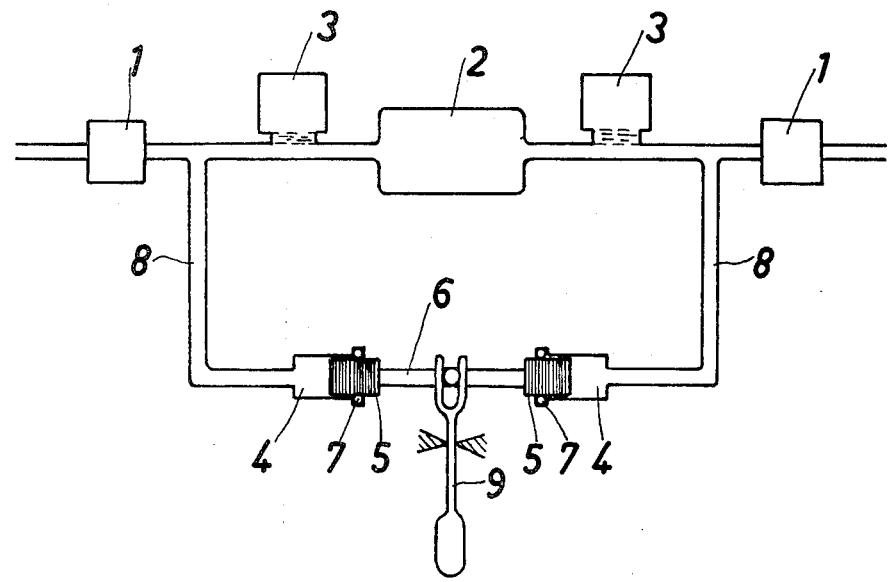

United States Patent [19]

Schütt et al.

[11] 4,203,817
[45] May 20, 1980

[54] METHOD OF AND DEVICE FOR MOVING LIQUID SAMPLES

[75] Inventors: Wolfgang Schütt, 141, Doberaner-Strasse; Hans-Ludwig Jensen, 6, Klosterbach-Strasse, both of, Rostock; Werner Eberlein, 5, Reinhold-Härzer-Strasse; Günter Schöppe, 24, Hans-Eisler-Strasse, both of, Jena, all of German Democratic Rep.

[73] Assignee: JENOPTIK JENA G.m.b.H., Jena, Fed. Rep. of Germany

[21] Appl. No.: 17,960

[22] Filed: Mar. 6, 1979

[51] Int. Cl.² .................... G01N 27/26; G01N 31/08
[52] U.S. Cl. ..................... 204/180 R; 204/180 G; 204/299 R; 137/86; 137/154; 137/205.5; 73/61.1 C
[58] Field of Search .......... 204/180 R, 299 R, 300 R; 73/53, 59, 61.1 C, 61.3; 137/42, 84, 85, 86, 154, 205.5

[56] References Cited

U.S. PATENT DOCUMENTS

| | | | |
|---|---|---|---|
| 2,064,627 | 12/1936 | Paine | 137/205.5 |
| 2,698,023 | 12/1954 | Eckman | 137/86 |
| 3,585,863 | 6/1971 | Hrdina | 73/61.1 C |
| 3,654,959 | 4/1972 | Kassel | 137/154 X |
| 3,690,340 | 9/1972 | Sipin | 137/205.5 X |
| 3,764,512 | 10/1973 | Greenwood et al. | 204/299 R |
| 3,793,180 | 2/1974 | Flower et al. | 204/299 R |
| 3,795,600 | 3/1974 | Allington | 204/180 G |
| 3,831,618 | 8/1974 | Liston | 137/154 |
| 3,948,607 | 4/1976 | Atwood et al. | 137/154 |

Primary Examiner—Arthur C. Prescott

[57] ABSTRACT

The invention is in concern of a method and a device for moving a liquid sample material in a measuring chamber, particularly for use in electrophoretic measurements. To permit precise measurements the remaining sample material is prevented from mixing with the sample material under test. The valves employed have to be closed in the course of the sample movement. This is realized in displacing the sample material by means of two pistons rigidly connected to each other and arranged in a by-pass of the measuring chamber.

3 Claims, 2 Drawing Figures

METHOD OF AND DEVICE FOR MOVING LIQUID SAMPLES

The invention relates to a method of and a device for feeding liquid samples by small amounts into a measuring chamber under elimination of any turbulence. The chamber is provided with an inlet and an outlet as being used in the course of microscopic observation of dispersed particles in a measuring cuvette, for example, in electrophoretic measurements.

To obtain a result in measurements of the kind mentioned hereinabove numerous particles which are dispersed in the sample material have to be investigated under identical measuring conditions. However, due to the particularities of the measuring device, only a few particles of the sample material can be investigated in a definite position.

In order to involve a greater number of particles at one time the sample material has to be moved by small amounts. In known devices the sample material is moved by a simultaneous opening and closing of valves or stopcocks.

The energy to move the sample is derived from the hydrostatic pressure.

Other devices displace the particles by supplying fresh sample material by means of pumps. Both devices have the disadvantage that the components which seal the system against ambience and which have to satisfy the highest requirements with respect of tightness are subject to the highest wear and hence do not ensure that fresh sample material having somewhat different physical properties, for example, temperature, index of pH, conductivity, is fed into the measuring cell. Furthermore, they do not permit a reproducible displacement of the sample material by a few micrometers.

It is an object of the invention to obviate the above disadvantages.

It is a further object of the invention to satisfy the highest precision measurements possible of a selected definite sample material.

It is still a further object of the invention to provide a method of and a device for moving a liquid sample material in a measuring chamber along a very small distance without introducing new sample material into the chamber and without the necessity of operating means such as valves or stopcocks for separating the sample material subject to test from the remainder.

It is still a further object of the invention to ensure a laminar flow in the course of the measuring operation.

The invention is concerned with a method of moving a liquid sample material in a measuring chamber by small amounts under elimination of any turbulence. The measuring chamber is provided with an inlet duct and an outlet duct, characterised in that the inlet duct and the outlet duct are closed and the sample material is displaced in a duct system connected to the inlet and outlet of the measuring chamber by means of a pair of pistons rigidly coupled to each other and operating in reverse directions.

The invention also includes a device for moving a liquid sample in a measuring chamber comprising a duct system, means for mechanically closing the inlet and outlet, in said duct system being arranged between said means, a measuring chamber, connected to the inlet duct and the outlet duct, two cylinders being symmetrically arranged to a common axis in a by-pass of said duct system and being of equal interiour diameter.

Each cylinder is provided with a piston being rigidly connected to each other by a common rod, having a central pivot for commonly moving the pistons in the respective cylinders, the front faces of the pistons contact the sample material averted from each other. The piston movements can be advantageously performed when rigidly connecting the pistons in direction of the movement to a spindle which meshes a rotatable nut.

Figure 2:
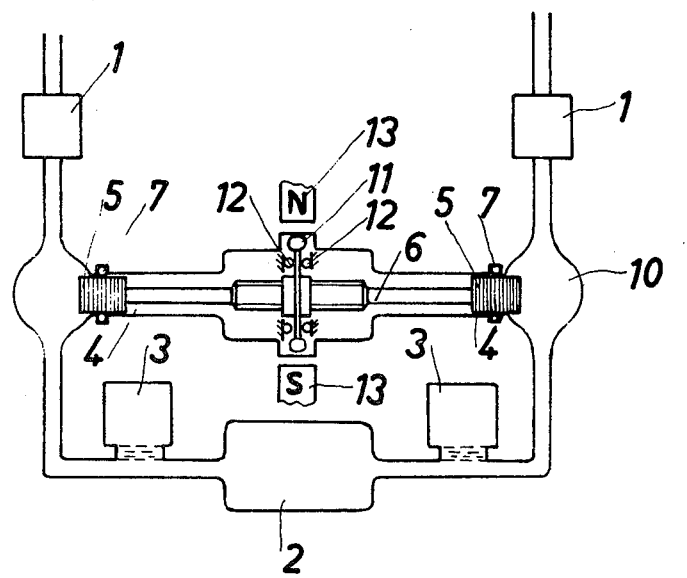

In order that the invention may be more readily understood reference is made to the accompanying drawings which illustrate diagrammatically and by way of example two embodiments thereof and where FIG. 1 is a schematic view of a first embodiment of a device for moving liquid sample material, FIG. 2 a schematic view of a second embodiment of a device for moving a liquid sample material.

In both embodiments like components are designated with like numerals.

In FIG. 1, in a duct system 8 two means 1, for example, valves are provided for closing or opening the system with respect to a not shown exteriour system. In said duct system 8 and between the two means 1 a measuring chamber 2, preferably a cuvette is provided. Two electrode cells 3 are arranged before, respectively, after the chamber 2 for applying an electric voltage to the sample material.

In a by-pass of the duct system 8 two cylinders are located subsequently and symmetrically to a common axis in parallel to the measuring chamber 2. In each cylinder 4 pistons 5 are displaceably arranged, electrically insulated from each other. The pistons 5 are rigidly connected to each other through a rod 6. Elements 7 are provided for air-tight sealing the pistons 5 relative to the cylinder 4 walls. A seated lever 9 commonly operates the pistons 5 via a fork portion hinged at A to the connecting rod 6. When the duct system 8 supplying the chamber 2 and the cylinders 4 with liquid sample material is filled by operating the means 1, an electrophoretic analyse can start. The sample material is moved within the chamber 2 by the common displacement of the pistons 5 via the lever 9.

In the embodiment of FIG. 2 the pistons 5 act upon the sample material in bulges 10 of the duct system 8. The rigid connection between the pistons 5 is embodied by a spindle 6 being the connecting element, which meshes a nut 11.

In rotating the nut seated in ball bearings 12 the sample material is moved. Very often particular requirements are set to the tightness of the tube system.

To this end the piston drive is entirely sealed and the nut 11 provided with respective coils is moved by external magnets 13.

We claim:

1. Method of moving liquid sample material in a measuring chamber by small amounts under elimination of any turbulence, said chamber being provided with an inlet duct and an outlet duct,
    comprising the steps of
    closing said inlet duct and outlet duct, and displacing said liquid sample material in a duct system by means of a reversely directed pair of pistons rigidly connected to each other.

2. A device for moving a liquid sample material in a measuring chamber by small amounts
    comprising
    a duct system for directing a liquid sample material, two valves for closing and opening said duct system to an exteriour duct system,
    said duct system being arranged inbetween said two valves,
    a measuring chamber being located in and being connected to said duct system by an inlet and an outlet opening,
two electrodes for applying a voltage to said liquid sample, and being located in said duct system adjacent to said inlet and to said outlet, respectively, of said measuring chamber,
a by-pass of said duct system, said by-pass branching off the duct system between the respective valves and the respective electrodes,
    said by-pass of said duct system opening into a first and into a second cylinder,
    said first and said second cylinder opposing each other in spaced relation and having a longitudinal axis in common, said first and said second cylinder being in parallel to said measuring chamber,
a first piston, having a front face,
a second piston, having a front face,
    said first piston being displaceably located in said first cylinder,
    said second piston being displaceably located in said second cylinder,
    said first piston and said second piston having equal diameters,
a rod, having a central pin,
    said rod rigidly connecting said first piston and said second piston symmetrically about said common longitudinal axis,
    said front face of said first piston being averted from said front face of said second piston,
a lever,
    being linked to said pin for commonly displacing said first and said second piston in said first and second cylinder via said rod.

3. Device for moving a liquid sample as claimed in claim 2, wherein the pistons are rigidly connected to a spindle in direction of movement and meshing a rotatable nut.

* * * * *